United States Patent
Funke et al.

(10) Patent No.: US 6,492,558 B2
(45) Date of Patent: Dec. 10, 2002

(54) PREPARATION OF N-BUTYLAMINES

(75) Inventors: Frank Funke, Mannheim (DE); Ulrich Steinbrenner, Neustadt (DE); Peter Zehner, Ludwigshafen (DE); Ralf Böhling, Griesheim (DE); Wolfgang Harder, Weinheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/025,539

(22) Filed: Dec. 26, 2001

(65) Prior Publication Data

US 2002/0169319 A1 Nov. 14, 2002

(30) Foreign Application Priority Data

Mar. 7, 2001 (DE) .......................... 101 10 842

(51) Int. Cl.[7] .............................. C07C 209/60
(52) U.S. Cl. ...................... 564/470; 564/485
(58) Field of Search ................. 564/470, 485

(56) References Cited

U.S. PATENT DOCUMENTS

| | | | |
|---|---|---|---|
| 2,501,556 A | 3/1950 | Whitman | 260/563 |
| 2,750,417 A | 6/1956 | Closson et al. | 260/577 |
| 3,758,586 A | 9/1973 | Coulson | 260/583 |
| 4,204,997 A | 5/1980 | Hobbs et al. | 260/326 |
| 4,302,603 A | 11/1981 | Pez | 546/485 |
| 4,336,162 A | 6/1982 | Pez | 252/438 |
| 4,454,321 A | 6/1984 | Gardner et al. | 546/184 |
| 4,582,904 A | 4/1986 | Wells et al. | 544/178 |
| 4,929,758 A | 5/1990 | Taglieber et al. | 564/485 |
| 5,763,668 A | 6/1998 | Dingerdissen et al. | 564/485 |
| 5,780,681 A | 7/1998 | Eller et al. | 564/485 |
| 5,892,125 A | 4/1999 | Kanand et al. | 568/449 |

FOREIGN PATENT DOCUMENTS

| | | |
|---|---|---|
| DE | 510 439 | 10/1930 |
| DE | 697372 | 10/1940 |
| DE | 2 117 970 | 10/1971 |
| DE | 195 24 242 | 1/1979 |
| DE | 36 34 247 | 7/1987 |
| DE | 196 24 206 | 1/1998 |
| EP | 0 039 918 | 11/1981 |
| EP | 0 054 746 | 6/1982 |
| EP | 132 736 | 2/1985 |
| EP | 200 923 | 11/1986 |
| EP | 0 752 409 | 1/1997 |
| EP | 822 179 | 2/1998 |
| FR | 1484782 | 9/1967 |
| GB | 1294 418 | 10/1972 |
| WO | 96/07630 | 3/1996 |

OTHER PUBLICATIONS

Möller "Erasatz von Aminogrupppen durch andere Aminogruppen" Shichslottrerbiudunger II vol. XI (1957) pp. 248–261.

Lehmkulh et al. "Katalytishce eaktionen von Aminen Mit Olefinen" J. Organometallic Chemistry vol. 55 (1973) pp. 215–220.

Steinborn et al. "Zur Komplexkatalyse der Aminomethylierung und Aminierung von Olefinen" Zietschrift für Chemie vol. 26 (1986) pp. 349–359.

Closson et al. "Base–Catalyzed Alkylation with Olefins" J. Am. Chem. Soc. vol. 22 (1936) pp. 646–649.

Pez et al. "Metal amide catalyzed lamination of olefins" Pure & Appl. Chem vol. 57, No. 12 (1985) pp. 1917–1926.

Brunet "Hydroamination of Alkenes, Amidorhodium Catalyst" Gazetta Chimica Italiana vol. 127 (1997) pp. 111–118.

Deeba et al. "Direct lamination of olefins: A comparative study over erionite and Y zeolites" Zeolites vol. 10 (1990) pp. 794–797.

Beller et al. "Basenkatalysierte Synthese on von N–(2–Arylethyl)anilenen und basenvermittelte Dominosynthese von 2,3–Dihydroinodolen" Angew. Chem. vol. 110 (1998) pp. 3571–3573.

Kakuno et al. "Addition of amines to conjugated dienes catalyzed by solid base catalyst" Jour. of Catalyst vol. 85 (1994) pp. 509–518.

Haak et al. "Katalytische Hydroaminierung von Alkenen und Alkinen" Organische Chemie vol. 5, (1999) pp. 297–303.

Müller et al. "Metal Initiated Amination of Alkenes and Alkynes" Chem. Rev. vol. 98 (1998) pp. 675–697.

Stroh et al. "Neuere Methoden der präparativen organischen Chemie" Angew Chem. vol. 69 (1957) pp. 124–131.

Howk et al. "Alkali–Metal Catalyzed Amination of Olefins" J. Am. Chem Soc. vol. 76 (1954) pp. 1899–1902.

Ullmann's Encyclopedia of Industrial Chemisty vol. A2 p. 4.

Steinborn et al., Z. Chem., vol. 29 (1989), pp. 333–334.

Primary Examiner—Brian J. Davis
(74) Attorney, Agent, or Firm—Keil & Weinkauf

(57) ABSTRACT

Process for the preparation of n-butylamines where n-butenylamines are firstly prepared by reacting 1,3-butadiene in the form of a 1,3-butadiene containing mixture obtained during the cracking of petroleum fractions or during the dehydrogenation of LPG or LNG or from GTL technology with a primary amine and/or a secondary amine under hydroaminating conditions, and the resulting butenylamine(s) are then reacted in a second process stage under hydrogenating and transalkylating conditions.

24 Claims, No Drawings

PREPARATION OF N-BUTYLAMINES

The present invention relates to processes for the preparation of n-butylamines and to the n-butenylamines which form as intermediate in this process.

n-Butylamines serve as starting materials for the preparation of surfactants, textile and flotation auxiliaries, bactericides, corrosion and foam inhibitors, additives for pharmaceuticals, and as antioxidants for fats and oils.

Alkylamines, such as butylamines, can be prepared by the hydrogenation of corresponding nitrites or nitro compounds, by the reductive amination of corresponding aldehydes and ketones and by the amination of corresponding alcohols.

The lower alkylamines ($C_{1-15}$-alkylamines), such as, for example, also butylamines (e.g. $C_4$–$C_{15}$-butylamines, such as n-butylamine, butylmethylamines, butylethylamines, butylisopropylamines and dibutylamines), are prepared industrially, in particular, by the amination of the corresponding alcohol or of the corresponding carbonyl compound with ammonia, a primary or secondary amine over metal catalysts which are e.g. supported, under hydrogenating conditions (see e.g.: Ullmann's Encyclopedia of Industrial Chemistry, Vol. A 2, $5^{th}$ Ed., page 4).

Alternatively, alkylamines, e.g. butylamines, can also be prepared over acidic phosphate catalysts from corresponding alcohols (see e.g. U.S. Pat. No. 4,582,904 (Air Products)).

A further alternative for the preparation of alkylamines, such as e.g. butylamines, consists in the addition of $NH_3$ or amines onto olefins in the presence of acidic catalysts, such as e.g. zeolites, see e.g. EP-A-132 736), in the presence of basic catalysts, such as e.g. metal amides, in particular alkali metal and alkaline earth metal amides (see e.g. B. W. Howk et al., *J. Am. Soc.* 76, page 1899ff (1954); R. Stroh et al., Angew. Chem. 69, 124ff (1957)), amides of subgroup IV (see e.g. D. Steinborn et al. (Z. Chem. 29 (1989), page 333ff) or alkali metal alkoxides, or in the presence of transition metal complex compounds (see e.g. U.S. Pat. No. 3,758,586).

EP-A-752 409 (DE-A-195 24 240) describes a process for the preparation of amines by hydroamination of olefin-containing mixtures obtained during the cracking of petroleum fractions, over zeolites, alumosilicates, phosphates, mesoporous oxides, Pillard clays, amorphous oxides or phyllosilicates. In particular, use is made here of butadiene-free C4 hydrocarbon mixtures (page 3, lines 10–12; Examples).

The processes listed above for the preparation of alkylamines have the following disadvantages:

The use of alcohols (e.g. ethanol), aldehydes, ketones and nitriles as starting materials for the preparation of alkylamines, such as butylamines, is significantly less economical on the basis of their costs than the use of corresponding olefins (e.g. ethene).

The use of olefins as starting material for the alkylamine preparation is accordingly desirable, but has hitherto been burdened with the following disadvantages (cf. e.g.: M. Beller et al., Chem. Rev. 98, 675f (1998) 675; R. Taube, "Reaction with Nitrogen Compounds" in B. Cornils and W. A. Hermann: "Applied Homogeneous Catalysis with Organometallic Compounds", VCH Weinheim, 1996, pages 507 to 520, and E. Haak et al., Chemie in unserer Zeit (1999), 297 to 303, in particular the summary on p. 302):

aa) The addition, under basic and heterogeneous catalysis, of amines onto olefins in the presence of metal oxide catalysts is possible, according to Kakuno et al., J. Catal. 85 (1984), page 509ff, with primary and secondary alkylamines, and conjugated dienes, such as butadiene or isoprene.

ab) The addition, under weakly basic catalysis, of amines onto olefins with alkali metal alkoxide as catalyst is, according to Beller et al., Angew. Chem. 110 (1998), page 3571ff, only successful in the case of aromatically conjugated amines and styrene as olefin component.

ac) In the case of the $NaNH_2$- or $KNH_2$-catalyzed addition of $NH_3$ onto olefins, as is described e.g. in B. W. Howk et al., J. Am. Chem. Soc. 76 (1954), 1899–1902 and R. D. Closson et al., U.S. Pat. No. 2,750,417, the space-time yields of desired alkylamines are very low even at high temperatures and olefin pressures amide.

ad) G. P. Pez (U.S. Pat. No. 4,336,162 and 4,302,603) describes a solution approach to the problem given in ac) by changing to the corresponding Rb and Cs amides or by using a eutectic of $NaNH_2$ and $KNH_2$. In the first case, industrial realization is precluded because of the extremely high cost of the catalyst, and in the second case the space-time yields of desired alkylamines are still too low.

b) Over acidic catalysts, such as e.g. zeolites, the addition of $NH_3$ onto olefins, ammonia generally being used in a high excess based on the olefin, does not proceed in every case with such good selectivities and yields for a certain alkylamine as, for example, in the case of isobutene (see e.g. DE-A-3634247).

The hydroamination of olefins with secondary amines in the presence of acidic catalysts again generally proceeds in poorer yields and with poorer selectivities than the corresponding hydroamination with ammonia or primary amines.

c) The transition metal complex-catalyzed hydroamination of olefins is generally possible in good yields only with secondary alkylamines (e.g.: Brunet, Gazzetta Chimica Italiana, 127, 1997, pages 111 to 118, page 112, left-hand column).

The two earlier German applications No. 10030619.5 from Jun. 28, 2000 and No. 10041676.4 from Aug. 24, 2000 describe a process for the preparation of alkylamines where, in a first process stage, an olefin is reacted with ammonia, a primary amine and/or a secondary amine under hydroaminating conditions, and then the resulting hydroamination product(s) is/are reacted in a second process stage under transalkylating conditions. The use of 1,3-butadiene in the form of a 1,3-butadiene-containing mixture obtained during the cracking of petroleum fractions or during the dehydrogenation of LPG or LNG or from GTL technology as olefin component is not disclosed herein.

A disadvantage of many processes for the preparation of amines from olefins is that the isolation of pure olefins or mixtures of pure olefins from mixtures obtained during the cracking of petroleum fractions is complex and expensive.

The complex separation of 1,3-butadiene from the C4 cut is described, for example, in K. Weissermel and H. -J. Arpe, Industrielle Organische Chemie [Industrial Organic Chemistry], 4th edition 1994, VCH Verlagsgesellschaft, page 76.

It is an object of the present invention to find, while overcoming the disadvantages of the prior art, an alternative, economical and flexible process for the preparation of n-butylamines which permits the preparation of a desired n-butylamine or two or more desired n-butylamines with high space-time yield and selectivity.

We have found that this object is achieved by a process for the preparation of n-butylamines which comprises firstly preparing n-butenylamines by reacting 1,3-butadiene in the form of a 1,3-butadiene-containing mixture obtained during the cracking of petroleum fractions or during the dehydrogenation of LPG or LNG or from GTL technology with a primary amine and/or a secondary mind under hydroaminating conditions and then reacting the resulting butenylamine(s) in a second process stage under hydrogenating and transalkylating conditions.

The 1,3-butadiene-containing mixtures preferably originate from the following sources:

a) C4 cuts which are produced on an industrial scale during the thermal or catalytic cleavage of petroleum fractions, such as, for example, petroleum spirits, in particular naphtha (steamcracking; see e.g. K. Weissermel and H. -J. Arpe, Industrielle organische Chemie [Industrial Organic Chemistry], 4th edition 1994, VCH Verlagsgesellschaft, pages 70–76);

b) hydrocarbon streams from the dehydrogenation of LPG or LNG, preferably $C^4$ cuts therefrom, where the C4 fraction of the LPG stream is separated off from the LPG stream before or after the dehydrogenation. A LNG stream with high C1 and C2 can here be converted beforehand into C4, for example via an MTO process.

Here, LPG means liquefied petroleum gas. Such liquefied gases are defined, for example, in DIN 51 622. They generally comprise the hydrocarbons propane, propene, butane, butene and mixtures thereof which are formed in oil refineries as secondary products during the distillation and cracking of petroleum, and in the processing of natural gas during the separation of petroleum spirit. LNG means liquefied natural gas. Natural gas consists primarily of saturated hydrocarbons which have varying compositions depending on their origin and are generally divided into three groups. Natural gas from pure natural gas deposits consists of methane and a small amount of ethane. Natural gas from petroleum deposits additionally comprises relatively large amounts of high molecular weight hydrocarbons, such as ethane, propane, isobutane, butane, hexane, heptane and secondary products. Natural gas from condensate and distillate deposits comprises not only methane and ethane, but also, to a considerable extent, higher-boiling components having more than 7 carbon atoms. For a more detailed description of liquefied gases and natural gas, reference is made to the corresponding keywords in Römpp, Chemielexikon, 9th edition.

The LPG and LNG used as feedstock includes, in particular, field butanes, as the C4 fraction of the "moist" fractions of natural gas, and of petroleum accompanying gases is called, which are separated off from the gases by drying and cooling to about –30° C. in liquid form. Low-temperature or pressure distillation thereof gives the field butanes, the composition of which varies depending on deposits, but which generally comprise about 30% isobutane and about 65% n-butane.

Suitable processes for the dehydrogenation of hydrocarbons are described, for example, in DE-A-100 47 642. In addition, for the dehydrogenation of alkanes, reference may be made to U.S. Pat. No. 4,788,371 WO 094/29021, U.S. Pat. No. 5,733,518, EP-A-0 838 534, WO 96/33151 or WO 096/33150.

The abovementioned MTO here means methanol-to-olefin. It is related to the MTG process (methanol-to-gasoline). This is a process for the dehydration of methanol over a suitable catalyst, giving an olefinic hydrocarbon mixture. Even $C_1$ feedstreams can thus, for example, be converted, via methanol and the MTO process, into olefin mixtures from which the $C_4$ fractions can be separated off by suitable methods. For example, separation can take place by distillation. For the MTO process, reference may be made to Weissermel, Arpe, Industrielle organische Chemie, 4th edition, 1994, VCH-Verlagsgesellschaft, Weinheim, p. 36 et seq..

The methanol-to-olefin process is also described, for example, in P. J. Jackson, N. White, Technologies for the conversion of natural gas, Austr. Inst. Energy Conference 1985.

c) C4 cuts from GTL Technology (GTL=gas to liquid), for example the Fischer-Tropsch synthesis.

d) All mixtures of the abovementioned hydrocarbon streams.

The preferred C4 cuts have the following composition (in % by weight):

1) C4 cracker cut:

1,3-butadiene: 25–60, preferably 35–50, particularly preferably 40–45, butenes (isobutene, 1-butene, trans-2-butene, cis-2-butene): 35–70, preferably 40–60, butanes (n-butane, isobutane): 3–12, preferably 5–10, alkynes (vinylacetylene, 1-butyne): 0–4, preferably 0–<2, particularly preferably 0–<1;

others (e.g. 1,2-butadiene, C5 components such as pentanes): 0–2, preferably 0–1.

A typical C4 cracker cut composition (in % by weight) is e.g.:

| | |
|---|---|
| 1,3-butadiene: | 42.3 |
| butenes: | 47.5 |
| butanes: | 8.7 |
| alkynes: | 0.8 |
| others: | 0.7 |

2) Hydrocarbon mixture from the dehydrogenation of n-butane:

1,3-butadiene: 3–40, preferably 5–30, particularly preferably 7–15;

butenes (1-butene, trans-2-butene, cis-2-butene): 25–70, preferably 35–60;

n-butane 25–70, preferably 35–60;

alkynes (vinylacetylene, 1-butyne): 0–1, preferably 0–0.5, particularly preferably 0–0.2;

others (e.g. 1,2-butadiene): 0–1, preferably 0–0.5.

A typical composition (in % by weight) of C4 cut from an n-butane dehydrogenation is e.g.:

| | |
|---|---|
| 1,3-butadiene: | 8 |
| butenes: | 46 |
| butanes: | 45 |
| others: | ≦1 |

3) Hydrocarbon mixture from the dehydrogenation of field butanes:

1,3-butadiene: 1–20, preferably 2–15, particularly preferably 3–10;

butenes (1-butene, trans-2-butene, cis-2-butene, isobutene): 45–85, preferably 55–80;

butanes (n-butane, isobutane): 10–50, preferably 15–40;

others 0–1, preferably 0–0.5.

A typical composition (in % by weight) of C4 cut from an n-butane dehydrogenation is e.g.:

| 1,3-butadiene: | 6 |
|---|---|
| butenes: | 66 |
| butanes: | 27 |
| others: | 1 |

Particular preference is given to using a C4 cut which comprises less than 2% by weight, in particular less than 1% by weight, of hydrocarbons which have a pKa value of less than 30, according to the MSAD scale.

Such hydrocarbons are e.g. 1-butyne and vinylacetylene.

[Definition of the MSAD scale ("Mc Ewen-Streitwieser-Applequist-Dessy scale") e.g. in D. J. Cram, Fundamentals of Carb Chemistry, Acad. press, 1965].

Surprisingly, using the process according to the invention, it is possible, in the reaction of the primary or secondary amine with the mixture containing 1,3-butadiene and further olefins, to react the amine with an olefin selectivity, based on all of the olefins in the mixture, of more than 90%, in particular more than 95%, very particularly more than 98%, with the 1,3-butadiene to give the corresponding n-butenylamine as hydroamination product. Thus, virtually only the 1,3-butadiene from the 1,3-butadiene-containing mixture reacts.

Particular preference is given to choosing the reaction conditions (see below) such that the 1,3-butadiene is removed completely (i.e. in an amount greater than 98%, in particular greater than 99%) from the 1,3-butadiene-containing mixture.

The constituents of the 1,3-butadiene-containing mixture used which remain after the reaction has been carried out can, following separation and optional purification, be further processed and used elsewhere. For example, these constituents which remain can be passed back to a steam-cracker again.

If the constituents of the 1,3-butadiene-containing mixture used which remain after the reaction has been carried out still comprise small amounts of 1,3-butadiene, these constituents can be returned to a 1,3-butadiene partial hydrogenation stage (K. Weissermel and H. -J. Arpe, Industrielle orsanische Chemie, 4th Ed. 1994, VCH Verlagsgesellschaft, page 76, 2nd paragraph).

In particular, the constituents of the 1,3-butadiene-containing mixture used which remain after the reaction has been carried out can, where removal of the 1,3-butadiene is complete as a result of the reaction, be further processed, following their separation, as raffinate I.

Such a raffinate I obtained according to the invention consists of n- butane, iso butane, 1-butene, cis-2-butene, trans-2-butene, isobutene, less than 1% by weight, in particular less than 0.5% by weight, very particularly 0–0.1% by weight, of 1,3-butadiene, 0–0.1% by weight of alkynes and optionally a further radical (e.g. traces of C5 components).

Prior to the further processing of the constituents of the 1,3-butadiene-containing mixture used which remain after the reaction has been carried out, these constituents may be purified by treatment with an acidic ion exchanger, an acidic heterogeneous catalyst (e.g. zeolite, acidic mixed oxide, γ-aluminum oxide), with dilute acid (extractive), or by distillation. This treatment removes, for example, any basic components still present, such as amine impurities.

In this respect, the process according to the invention is also a process for the preparation of a 1,3-butadiene-free mixture (i.e. 1,3-butadiene content of less than 1% by weight, in particular less than 0.5% by weight, very particularly less than 0.1% by weight), e.g. raffinate I, from the corresponding 1,3-butadiene-containing mixture obtained during the cracking of petroleum fractions or during the dehydrogenation of LPG or LNG or from GTL technology (e.g. a C4 cut).

Depending on the chosen reaction conditions (see below), it is possible for some of the 1-butene present in the 1,3-butadiene containing mixture to also react with the primary and/or secondary amine. Since this likewise leads to desired n-butylamines, this "secondary reaction" is not disadvantageous.

Primary and secondary amines which can be used in the process according to the invention, or mixtures thereof, are generally amines of the formula

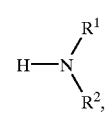

II in which
R$^1$ is hydrogen (H), alkyl, in particular C$_1$–C$_{20}$-alkyl, alkenyl, in particular C$_2$–C$_{20}$-alkenyl, cycloalkyl, in particular C$_3$–C$_{20}$-cycloalkyl, alkoxyalkyl, aminoalkyl, monoalkylaminoalkyl, dialkylaminoalkyl, aryl, aralkyl and R$^2$ is alkyl, in particular C$_1$–C$_{20}$-alkyl, alkenyl, in particular C$_{2-C20}$-alkenyl, cycloalkyl, in particular C$_3$–C$_{20}$-cycloalkyl, alkoxyalkyl, aminoalkyl, monoalkylaminoalkyl, dialkylaminoalkyl, aryl, aralkyl, and R$^1$ and R$^2$ together may be a saturated or unsaturated C$_3$- to C$_9$-alkylene chain which may be interrupted by an O, S or N heteroatom, in particular together may be a —(CH$_2$)$_j$—X—(CH$_2$)$_k$— group, where j and k=1 to 4 and X=CH$_2$, CHR$^3$, oxygen (O), sulfur (S) or NR$^3$, where R$^3$=H or C$_1$–C$_4$-alkyl.

Examples of primary amines according to formula II are methylamine, ethylamine, n-propylamine, isopropylamine, n-butylamine, isobutylamine, tert-butylamine, n-pentylamine, cyclopentylamine, isopentylamine, n-hexylamine, cyclohexylamine, n-octylamine, n-decylamine, 1-phenylethylamine, 2-phenylethylamine, allylamine, 2-dimethylaminoethylamine and 2-methoxyethylamine.

Examples of secondary amines according to formula II are dimethylamine, diethylamine, di-n-propylamine, diisopropylamine, di-n-butylamine, pyrrolidine, piperidine, hexamethylenamine, piperazine and morpholine.

The catalyst used in the preparation of n-butenylamines by reacting 1,3-butadiene in the form of a 1,3-butadiene-containing mixture obtained during the cracking of petroleum fractions with a primary or secondary amine is an alkali metal, a metal monoalkylamide or metal dialkylamide, a metal amide corresponding to the amine used or a transition metal complex compound.

Alkali metals, in particular Na and K, very particularly Na, are preferred as catalysts.

The alkali metal reacts in situ with the primary and/or secondary amine and the 1,3-butadiene to give the corresponding alkali metal amide.

With regard to the metal amide catalysts, metal dialkylamides are preferred over metal monoalkylamides.

The metal monoalkylamides and metal dialkylamides generally have the formula MNR$^4$R$^5$ (M=monovalent metal), M(NR⁴R⁵)₂ (M=divalent metal), M(NR⁴R⁵)₃ (M=trivalent metal) or M(NR⁴R⁵)₄ (M=tetravalent metal), where R⁴ has the meanings according to the radical R¹ and R⁵ has the meanings according to the radical R², and R⁴ and R⁵ may also together be a saturated or unsaturated C₃–C₉-alkylene chain which may be interrupted by an O, S or N heteroatom (as defined for R¹ and R²), in particular may together be a —(CH₂)ⱼ—X—(CH₂)ₖ— group (as defined for R¹ and R²) (see above).

The metal amides particularly preferably have the formula MNR¹R², M(NR¹R²)₂, M(NR¹R²)₃ or M(NR¹R²)₄, in which, accordingly, the radicals R correspond to those of the primary and/or secondary amine used.

As metal component (M) in the metal monoalkylamide and metal dialkylamide catalysts, preference is given to metals of groups IA, IIA, IIIB and IVB (Li, Na, K, Rb, Cs, Mg, Ca, Sr, Ba, Sc, Y, La or a lanthanide element, Ti, Zr or Hf), in particular Li, Na, Mg, Ca and K, very particularly Na and K.

Examples of such metal alkylamides are NaHNEt, NaNEt₂, KHNEt, KNEt₂, LiHNEt, LiNEt₂, LiN(iso-C₃H₇)₂, NaN(iso-C₃H₇)₂, NaN(n-C₄H₉)₂, NaHN(iso-C₃H₇), NaHN (isopentyl), Mg(NEt₂)₂, Ca(NPr₂)₂ and Zr (NEt₂)₄.

In the case of the hydroamination of di-n-butylamine with the 1,3-butadiene-containing mixture, NaN(n-BU)₂ and KN(n-Bu)₂ are particularly preferred, and in the case of that of n-butylamine with the 1,3-butadiene-containing mixture, Na(H)N(n-Bu) and K(H)N(n-Bu) are particularly preferred.

These metal amides are prepared as described in Houben-Weyl, Methoden der organischen Chemie [Methods of Organic Chemistry], 4th edition, Volume XI/2 (nitrogen compounds II and III), Verlag Thieme, Stuttgart, p. 182ff, in U.S. Pat. No. 4,595,779, WO 93/14061, DE-A-21 17 970, DRP 615,468, GB-A-742 790, DE-A-26 13 113, U.S. Pat. No. 2,750,417, J. Wollensak, Org. Synth. 43 (1963), page 45ff, or C. A. Brown, J. Am. Chem. Soc. 95(3) (1973), page 982ff, by reacting metal with the corresponding amine in the presence of an unsaturated compound such as, for example, butadiene, isoprene, naphthalene, pyridine or styrene, by reacting a metal amide or hydride with the corresponding amine or by reacting an organometallic compound, such as, for example, n-BuLi, MeLi, PhNa, Et₂Mg or Et₄Zr, with the corresponding amine.

The transition metal complex compound used as catalyst is generally a complex compound of a metal of group IIIB, IVB or VIII of the Periodic Table of the Elements.

Examples thereof are the rhodium or iridium compounds described in U.S. Pat. No. 3,758,586, such as (cyclooctadiene)₂RhCl₂, RhCl₃, RhBr₃ and IrCl₃, for the reaction of secondary aliphatic amines, the ruthenium and iron compounds described in U.S. Pat. No. 4,454,321, such as RuCl₃*xH₂O, Ru(cyclopentadienyl)₂, [Ru(NH₃)₄(OH)Cl]Cl*2 H₂O, Fe(CO)₅, Fe₂(CO)₉, H₂Fe(CO)₄, Fe(butadiene) (CO)₃, Fe(CO)₅/tri-n-butylphosphine, Fe(CO)₅/triphenyl phosphite, for the reaction of primary or secondary amines, the platinum and palladium compounds cited in the overview article by Th. E. Müller and M. Beller in Chem. Rev. 1998, Vol. 98, No. 2, pages 675 to 703, on pages 679 to 680, such as PtX₄²⁻ (X=Cl⁻, Br⁻), the lanthanum, neodymium, samarium and lutetium compounds cited in the abovementioned overview article by Th. E. Müller and M. Beller on pages 681 to 684, such as Cp*₂Ln–E (Cp*=pentamethylcyclopentadienyl or tetramethylcyclopentadienyl with bridge to the second tetramethylcyclopentadienyl ligand, Ln=La, Nd, Sm or Lu, E=H, CH(SiMe₃)₂ or N(SiMe₃)₂), and the platinum, ruthenium, hafnium, zirconium, iridium and tantalum compounds cited in the abovementioned overview article by Th. E. Müller and M. Beller on pages 684 to 686, such as Pt(PEt₃)₂(H)(NHPh), IrCl(C₂H₄)₂ (PEt₃)₂ and Cp₂Zr(H)[N(t-Bu)(SiHMe₂)].

The process for the preparation of the n-butenylamines can be carried out as follows:

1,3-butadiene (I) in the form of a 1,3-butadiene-containing mixture obtained during the cracking of petroleum fractions or during the dehydrogenation of LPG or LNG or from GTL technology, preferably in the form of a 1,3-butadiene-containing mixture with a composition as described above, is reacted with a primary amine and/or a secondary amine under hydroaminating conditions (hydroamination).

The reaction generally takes place according to the following reaction scheme.

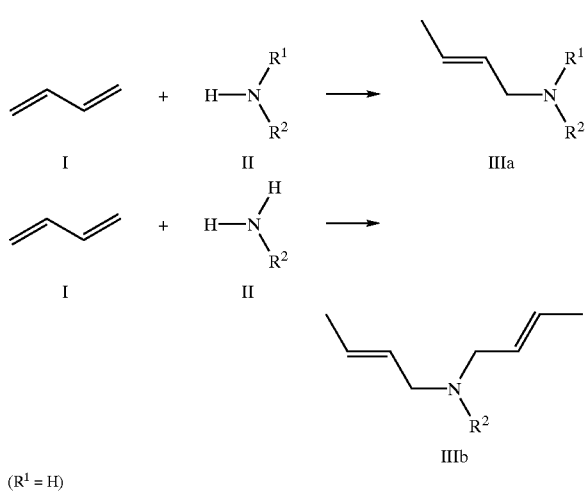

(R¹ = H)

In the case of the reaction of the 1,3-butadiene-containing mixture with a secondary amine, an n-butenylamine IIIa results as tertiary amine in the hydroamination stage.

In the case of the reaction of the 1,3-butadiene-containing mixture with a primary amine, either an n-butenylamine IIIa results as secondary amine (R¹=H) or a di-n-butenylamine IIIb results as tertiary amine, or a mixture thereof, depending on the reaction conditions chosen in the hydroamination stage.

To simplify the above scheme, it has been assumed that in the hydroamination of the 1,3-butadiene, the resulting olefinic double bond is neither in the α position, nor in the β position, nor in the δ position, relative to the nitrogen in III (corresponding to an imine or enamine or homoallylamine, respectively). However, in this process stage, it is entirely possible for double bond isomerization to occur under the basic conditions.

Very particularly preferred amines are mono- and dialkylamines, such as monoethylamine, diethylamine, n-butylamine, di-n-butylamine and isopropylamine.

The hydroamination products starting from the 1,3-butadiene and n-butylamine are n-butenyl-n-butylamine and di-n-butenyl-n-butylamine, and, starting from the 1,3-butadiene and di-n-butylamine, di-n-butyl-n-butenylamine.

a) Alkali Metal and Metal Amide Catalysis

The reaction of the 1,3-butadiene-containing mixture with the amine in the presence of the metal amide (hydroamination stage) can be carried out analogously to the description in G. P. Pez et al., Pure & Appl. Chem. 57(12), 1917–26 (1985), R. D. Closson et al., J. Org. Chem. 22 (1957), 646–9, G. M. Whitman et al., U.S. Pat. No. 2,501, 556), D. Steinborn et al., Z. Chem. 29 (1989), 333–4, D. Steinborn et al., Z. Chem. 26 (1986) 349–59 and H. Lehmkuhl et al., J. Organomet. Chem. 55 (1973), 215–20.

The reaction of the 1,3-butadiene-containing mixture with the amine in the presence of the metal amide can also be carried out in the presence of small amounts of ammonia (less than 1 mol % based on the amine(s) used) (cf. analogous to DE-A-21 17 970).

The preparation of the metal amide and the catalytic hydroamination of the 1,3-butadiene-containing mixture can also be carried out in a "one-pot synthesis", i.e. simultaneously.

For this, use is made of an organometallic compound, e.g. BuLi, and the amine, e.g. di-n-butylamine, or (preferably) an alkali metal, e.g. Na, and the amine, e.g. di-n-butylamine.

The alkali metal is preferably used here in dispersed and/or suspended form, in particular in a particle size (diameter) of from 0.1 to 1000 $\mu$(micrometers). The preparation of such alkali metal dispersions or suspensions is carried out in accordance with methods known to the person skilled in the art, e.g. by appropriate action of shear forces, such as e.g. stirring or ultrasound. (Cf. e.g. "Organikum" [Organic Chemistry], 2nd reprint of the 15th edition, page 584, VEB Verlag 1981).

The metal amide can be converted into metal hydride during the reaction by $\beta$-elimination or the action of $H_2$ as described in DE-A-26 13 113; in the case of the $\beta$-elimination, an imine arises in parallel in the process. This can be converted back into a metal amide and $H_2$ under the action of a primary or secondary amine, in accordance with DE-A-26 13 113, C. A. Brown, J. Am. Chem. Soc. 95(3) (1973), 982ff or C. A. Brown, Synthesis (1978), 754ff, meaning that the metal hydride can be regarded as a type of "rest form" of the metal amide and, for the purposes of the present invention, is therefore to be equated with the metal amide.

In addition, complexing agents may be present as solvents both during the preparation of the catalyst and also during the hydroamination reaction.

Thus, e.g. J. F. Remenar (J. Am. Chem. Soc. 120 (1988), 4081ff), H. Lehmkuhl et al. (J. Organomet. Chem. 55 (1973), 215ff) and D. Steinborn et al. (Z. Chem. 29 (1989), 333ff) describe the use of N,N,N',N'-tetramethylethylenediamine, N,N,N',N'',N''-pentamethyldiethylenetriamine, N,N,N',N'-tetramethylcyclohexanediamine and tetrahydrofuran as complexing agent.

In addition, amines with two or more aminic N atoms per molecule, such as, for example, N,N,N',N'-tetraethylethylenediamine, N-permethylated or N-perethylated tetraethylenetetramine up to N-permethylated or N-perethylated polyimine having molar masses up to 500 000 daltons, ethers and polyethers, such as e.g. diglymes, triglymes and the corresponding homologs, terminally capped polyols—e.g. PEG, PPG, poly—THF—, and complexing agents with aminic N and etheric O atoms in the molecule, such as e.g. 3-methoxyethylamine, 3-(2-methoxyethoxy)propylamine or N,N,N',N'-tetramethyldiaminodiethyl ether, may be present.

The procedure generally involves dissolving or suspending the catalyst [or the corresponding alkali metal or the corresponding metal hydride or the corresponding organometallic compound (e.g. n-BuLi), in each case as catalyst "precursor"] in a primary and/or secondary amine, particularly preferably in a secondary amine.

The catalyst may be present as a solution, a suspension, or in supported form on a typical catalyst support, such as e.g. $SiO_2$, $Al_2O_3$, $TiO_2$, $ZrO_2$, activated carbon, MgO, $MgAl_2O_4$. The catalyst is preferably in the form of a solution or suspension, particularly preferably a solution.

The hydroamination of the 1,3-butadiene-containing mixture can be carried out batchwise, semicontinuously or continuously.

In the first case, the 1,3-butadiene-containing mixture is added to catalyst and amine and reacted. In the second case, the 1,3-butadiene-containing mixture is metered into the reaction mixture. In the third case, catalyst, amine and 1,3-butadiene-containing mixture are metered in continuously.

Preference is given to a molar ratio of 1,3-butadiene-containing mixture: secondary amine of 3:1 to 1:10, particularly preferably 1:1 to 1:2.

Preference is given to a molar ratio of 1,3-butadiene-containing mixture: primary amine of 6:1 to 1:5, particularly preferably 2:1 to 1:1.

The reaction is carried out, preferably with stirring, at 0 to 250° C., in particular at 20 to 150° C. and particularly preferably at 40 to 120° C.

The reaction can be carried out under the pressure which arises under the chosen conditions (autogenous pressure). Generally, the pressure while the reaction is being carried out is from 0 to 200 bar above atmospheric, in particular 2 to 100 bar, very particularly 3 to 30 bar.

Suitable reactors are all typical reaction apparatuses, e.g. stirred reactors, loop reactors, bubble columns, packed bubble columns, cascaded bubble columns and stirred columns.

After the reaction, the product is separated off from the catalyst, e.g. by distillation, rectification, filtration, membrane filtration, washing with water or adsorption.

Catalyst (metal amide or metal hydride) which has not undergone protolysis can then be recycled.

b) Transition Metal Complex Compound Catalysis

The reaction of the 1,3-butadiene-containing mixture with the primary and/or the secondary amine can be carried out, for example, as described in the literature given above in the discussion of the transition metal complex compounds.

The reaction can be carried out continuously, batchwise or semi-batchwise.

In the batchwise procedures, the catalyst is introduced together with the amine. After the reaction temperature has been reached, the 1,3-butadiene-containing mixture is injected in. When the pressure has decreased (measure of the reaction), the product or product mixture is distilled off.

Excess 1,3-butadiene and unreacted amine can be recycled.

In the batchwise procedure the catalyst, together with the product mixture, can be conveyed out of the reactor via the bottom and worked up separately.

The reaction can be carried out in a stirred reactor.

In the case of the continuous procedure, the reaction can be carried out in a bubble column. Here, the 1,3-butadiene-containing mixture is blown from below through the mixture of catalyst and product solution. The solution can then be removed from the catalyst by distillation or the catalyst can be removed from the product solution by means of a membrane. Alternatively, the catalyst does not need to be removed but can be passed directly to the work-up or to the next process stage, provided it does not cause interference there.

Second Process Stage

Following the reaction of the 1,3-butadiene-containing mixture with the primary and/or secondary amine under hydroaminating conditions, the resulting hydroamination product(s) is(are) reacted in a second process stage under transalkylating conditions.

Variant a)

The process products of the transalkylation in this second process stage are again n-butenylamines. The composition of the reaction discharge of this transalkylation stage differs from that of the preceding hydroamination stage by the fact that, inter alia, the n-butenylamines obtained as products are present in a different molar ratio relative to one another.

This second process stage is preferably carried out in the presence of a transalkylation catalyst.

Preferred temperatures for this amine transalkylation stage are 80 to 400° C.

The reaction discharge from the first hydroamination stage can, usually following removal of the catalyst (as described above in each case), be used directly in this second process stage.

However, it is also possible to firstly separate off the n-butenylamine(s) as hydroamination product(s) from the reaction discharge of the first hydroamination stage which is/are desired for this second process stage (as described above in each case), and then to use it/them in this second process stage.

Advantageously, for the second process stage, ammonia and/or amines can also be passed to the feed, and/or ammonia and/or amines from the reaction discharge can be passed (returned) to this second process stage.

In a preferred embodiment, the product mixture obtained in the second process stage (transalkylation stage) is separated into (a) product(s) which is/are returned to the first process stage (hydroamination stage), and/or (a) product(s) which is/are returned to the second process stage (transalkylation stage), and the desired n-butenylamine(s).

The reaction of the hydroamination product/products obtained in the first process stage in the second process stage under transalkylating conditions can be carried out, for example, as described in Houben Weyl Volume XI/1, Nitrogen compounds II, 1957, Georg Thieme Verlag Stuttgart, pp. 248–261.

Accordingly, the amine transalkylation ("amine exchange") can be carried out in the presence of transalkylation catalysts, such as acids, zeolites, metal salts, iodine, dehydration catalysts, hydrogenation/dehydrogenation catalysts or else in the absence of catalysts.

Acids suitable as transalkylation catalyst are, for example, hydrohalic acids (such as HCl), phosphoric acid, sulfanilic acid or sulfonic acids (such as p-toluenesulfonic acid).

Zeolites suitable as transalkylation catalyst are, for example, faujasites, such as X, Y and USY zeolites, erionite, chabazite, mordenite, offretite, clinoptiolite, pentasiles such as ZSM-5 and ZBM-10, ZSM-11, ZSM-12, MCM-22, MCM-41, MCM-48, MCM-49, MCM-56, EMT, SSZ-26, SSZ-33, SSZ-37, CIT-1, PSH-3, NU-85, beta and the boron-containing forms, such as, for example, ZBM-11, H-boron-ZSM-5, H-boron-beta, H-boron-ZSM-11, and the gallium- or titanium-containing forms. They are characterized by a high number of catalytically active centers, combined with a large surface area.

These zeolites differ in type and in the nature of the aftertreatment following their preparation (e.g. thermal treatment, dealuminization, acid treatment, metal ion exchange, etc.).

Examples of suitable zeolites are given in U.S. Pat. No. 4,375,002, 4,536,602, EP-A-305 564, EP-A-101 921 and DE-A-42 06 992.

Also suitable are the zeolites known from EP-A-133 938, EP-A-431 451 and EP-A-132 736, which are borosilicate, gallosilicate, alumosilicate and ferrosilicate zeolites, which may optionally be doped as described with alkali metals, alkaline earth metals and transition metals.

Also suitable are, for example, the beta zeolites known from CA-A-2 092 964, which are defined as crystalline alumosilicates of certain composition with a pore size of more than 5 Å.

Preference is given to using metal- or halogen-modified beta zeolites, as described, for example, in DE-A-195 30 177.

Also particularly suitable are zeolite catalysts of the pentasil type having a $SiO_2/Al_2O_3$ molar ratio of greater than or equal to 10, as are disclosed in EP-A-132 736.

Metal salts suitable as transalkylation catalyst are, for example, zinc or iron halides, such as zinc chloride, iron(II) chloride or iron(III) chloride.

Dehydration catalysts suitable as transalkylation catalyst are, for example, manganese(II) oxide/activated carbon, alumosilicates, $Al_2O_3$, $TiO_2$ or $ZrO_2$.

As transalkylation catalyst, preference is given to hydrogenation and dehydrogenation catalysts.

In this connection, the presence of hydrogen is advantageous to maintain the catalytic activity. Alternatively, the hydrogenation or dehydrogenation catalyst can be freed from deposits by reduction with $H_2$ at regular intervals.

Particularly suitable hydrogenation and dehydrogenation catalysts are catalysts which contain, as catalytically active constituents, elements chosen from the group consisting of copper, silver, gold, iron, cobalt, nickel, rhenium, ruthenium, rhodium, palladium, osmium, iridium, platinum, chromium, molybdenum and tungsten, in each case in metallic form (oxidation state 0) or in the form of compounds such as, for example, oxides, which are reduced to the corresponding metal under the process conditions.

The catalytically active constituents copper, silver, gold, iron, cobalt, nickel, rhenium, ruthenium, rhodium, palladium, osmium, iridium, platinum, chromium, molybdenum and/or tungsten are generally present in the catalytically active mass of the catalyst in overall amounts of from 0.1 to 80% by weight, preferably 0.1 to 70% by weight, particularly preferably 0.1 to 60% by weight, calculated as metal in oxidation state 0.

Preference is given to catalysts which contain, as catalytically active constituents, elements chosen from the group consisting of copper, silver, nickel, ruthenium, rhodium, palladium, platinum, chromium and molybdenum, in particular chosen from the group consisting of copper, cobalt, nickel, in each case in metallic form (oxidation state 0) or in the form of compounds, such as, for example, oxides, which are reduced to the corresponding metal under the process conditions.

More preference is given to catalysts which contain the catalytically active constituents copper, silver, iron, cobalt, nickel, ruthenium, rhodium, palladium, osmium, iridium and/or platinum and a support material, preferably chosen from the group consisting of aluminum oxide, zirconium dioxide, titanium dioxide, carbon and/or oxygen-containing compounds of silicon.

The catalytically active mass of these catalysts preferably used in the process according to the invention comprises the catalytically active constituents copper, silver, iron, cobalt, nickel, ruthenium, rhodium, palladium, osmium, iridium and/or platinum generally in overall amounts of from 0.1 to 80% by weight, preferably 0.1 to 70% by weight, particularly preferably 0.1 to 60% by weight, calculated as metal in oxidation state 0.

Furthermore, the catalytically active mass of these preferably used catalysts comprises the support materials aluminum oxide ($Al_2O_3$), zirconium dioxide ($ZrO_2$), titanium dioxide ($TiO_2$), carbon and/or oxygen containing compounds of silicon, calculated as $SiO_2$, generally in coverall amounts of from 20 to 99.9% by weight, preferably 30 to 99.9% by weight, particularly preferably 40 to 99.9% by weight.

Particular preference is given to catalysts with the active compounds Cu, Co, Ni and/or Pd, in particular Cu, Co and/or Ni. These can be used as unsupported catalysts or as supported catalysts.

Very particular preference is given to Cu-containing catalysts which, as has been recognized according to the invention, are more selective because of their comparatively low ethane and methane formation.

Examples thereof are copper alloys, metallic copper, e.g. in the form of copper gauze, and Cu catalysts with a Cu content of from 2 to 70% by weight of Cu, calculated as CuO, on a support, preferably with 10 to 55% by weight of Cu, calculated as CuO, on a support. Preferred support materials may be aluminum oxide ($Al_2O_3$), zirconium dioxide ($ZrO_2$), titanium dioxide ($TiO_2$), carbon and/or oxygen-containing compounds of silicon.

For example, catalysts disclosed in EP-A-382 049 whose catalytically active mass prior to treatment with hydrogen comprises 20 to 85% by weight, preferably 70 to 80% by weight, of $ZrO_2$, 1 to 30% by weight, preferably 1 to 10% by weight, of CuO, and in each case 1 to 40% by weight, preferably 5 to 20% by weight, of CoO and NiO, for example the catalysts described in loc. cit. on page 6 and having the composition 76% by weight of Zr, calculated as $ZrO_2$, 4% by weight of Cu, calculated as CuO, 10% by weight of Co, calculated as CoO, and 10% by weight of Ni, calculated as NiO, can be used in the process according to the invention.

In addition, the catalysts disclosed in EP-A-963 975 whose catalytically active mass prior to treatment with hydrogen comprises 22 to 40% by weight of $ZrO_2$, 1 to 30% by weight of oxygen-containing compounds of copper, calculated as CuO, 15 to 50% by weight of oxygen-containing compounds of nickel, calculated as NiO, where the Ni:Cu molar ratio is greater than 1, 15 to 50% by weight of oxygen-containing compounds of cobalt, calculated as CoO, 0 to 10% by weight of oxygen-containing compounds of aluminum and/or manganese, calculated as $Al_2O_3$ or $MnO_2$, respectively, and does not comprise oxygen-containing compounds of molybdenum, for example catalyst A disclosed in loc. cit., page 17, and having the composition 33% by weight of Zr, calculated as $ZrO_2$, 28% by weight of Ni, calculated as NiO, 11% by weight of Cu, calculated as CuO and 28% by weight of Co, calculated as CoO, can be used in the process according to the invention.

In addition, catalysts disclosed in EP-A-514 692 whose catalytically active mass prior to treatment with hydrogen comprises 5 to 100% by weight of an oxide of copper and nickel in the atomic ratio from 1:1 to 10:1, preferably from 2:1 to 5:1, and zirconium oxide and/or aluminum oxide, in particular the catalysts disclosed in loc. cit. on page 3, lines 20 to 30, whose catalytically active mass prior to treatment with hydrogen comprises 20 to 80% by weight, particularly 40 to 70% by weight, of $Al_2O_3$ and/or $ZrO_2$, 1 to 30% by weight of CuO, 1 to 30% by weight of NiO and 1 to 30% by weight of CoO, can be used in the process according to the invention.

Preferably, catalysts disclosed in DE-A-19 53 263 and comprising cobalt, nickel and copper and aluminum oxide and/or silicon dioxide with a metal content of from 5 to 80% by weight, in particular 10 to 30% by weight, based on the overall catalyst, where the catalysts comprise, calculated on the metal content, 70 to 95% by weight of a mixture of cobalt and nickel and 5 to 30% by weight of copper, and where the weight ratio of cobalt to nickel is 4:1 to 1:4, in particular 2:1 to 1:2, the catalysts disclosed in EP-A-696 572 whose catalytically active mass prior to reduction with hydrogen comprises 20 to 85% by weight of $ZrO_2$, 1 to 30% by weight of oxygen-containing compounds of copper, calculated as CuO, 30 to 70% by weight of oxygen-containing compounds of nickel, calculated as NiO, 0.1 to 5% by weight of oxygen-containing compounds of molybdenum, calculated as $MoO_3$, and 0 to 10% by weight of oxygen-containing compounds of aluminum and/or manganese, calculated as $Al_2O_3$ or $MnO_2$, respectively, for example the catalyst disclosed in loc. cit., page 8, having the composition 31.5% by weight of $ZrO_2$, 50% by weight of NiO, 17% by weight of CuO and 1.5% by weight of $MoO_3$, the catalysts disclosed in EP-A-284 919 and of the formula $M_xMg_y(SiO_2)\cdot nH_2O$, in which M is a divalent, reducible metal atom from the group consisting of Cu, Fe, Co and Ni, x and y are numbers which together can reach the value 1.5, and n, after drying and expressed in % by weight, is between 0 and 80, for example the catalyst described in loc. cit. in the example, comprising 35% CuO, 9% MgO and 38% $SiO_2$, and the catalyst described in EP-A-863 140 on page 3, comprising 45 to 47% by weight of CuO, magnesium silicate from about 15 to 17% by weight of MgO and 35 to 36% by weight of $SiO_2$, approximately 0.9% by weight of $Cr_2O_3$, approximately 1% by weight of BaO and approximately 0.6% by weight of ZnO, the catalysts disclosed in DE-A-24 45 303 which are obtainable by heat-treating a basic copper- and aluminum-containing carbonate of the composition $Cu_mAl_6(CO_3)_{0.5m}O_3(OH)_{m+12}$, where m is any value, including fractions, between 2 and 6, at a temperature of from 350 to 700° C., for example the copper-containing precipitation catalyst disclosed in loc. cit., Example 1, which is prepared by treating a solution of copper nitrate and aluminum nitrate with sodium bicarbonate and subsequently washing, drying and heat-treating the precipitate, and the supported catalysts disclosed in WO 95/32171 and EP-A-816 350, comprising 5 to 50% by weight, preferably 15 to 40% by weight, of copper, calculated as CuO, 50 to 95% by weight, preferably 60 to 85% by weight, of silicon, calculated as $SiO_2$, 0 to 20% by weight of magnesium, calculated as MgO, 0 to 5% by weight of barium, calculated as BaO, 0 to 5% by weight of zinc, calculated as ZnO, and 0 to 5% by weight of chromium, calculated as $Cr_2O_3$, in each case based on the total weight of the calcined catalyst, for example the catalyst disclosed in EP-A-816 350, page 5, comprising 30% by weight of CuO and 70% by weight of $SiO_2$, can be used according to the invention.

The hydrogenation or dehydrogenation catalysts used as transalkylation catalyst in the process according to the invention can be prepared by processes described in the prior art, and some of them can also be obtained commercially.

In the case of the preparation of supported catalysts, no limitations of any kind exist with regard to the method of applying the active components, such as, for example, nickel, cobalt and/or copper and optionally further components, to the support material used.

Particularly suitable application methods are impregnation and precipitation, e.g. as described in the earlier German application No. 10041676.4 from Aug. 24, 2000, pages 26–28.

Variant b)

In a preferred embodiment, following the reaction of the 1,3-butadiene-containing mixture with the primary and/or secondary amine under hydroaminating conditions, the resulting hydroamination product(s) is/are reacted in a second process stage under transalkylating and hydrogenating conditions.

If the reaction in the second process stage is carried out under transalkylating and simultaneous hydrogenating conditions, in particular in the presence of hydrogen and a transalkylating hydrogenation or dehydrogenation catalyst, the n-butenylamines present in the hydroamination discharge from the first process stage and optionally further unsaturated organic nitrogen compounds, i.e. organic nitrogen compounds which either have an olefinic C=C double bond (e.g. as in enamines) or are imines, can be hydrogenated to the correspondingly saturated n-butylamines.

Preferred transalkylating hydrogenation or dehydrogenation catalysts here are the same hydrogenation and dehydrogenation catalysts as have already been described above for variant a).

The hydroamination discharge from the first process stage comprises e.g., in addition to the n-butenyl function in the n-butenylamines, further unsaturated functions if the amine used in the first process stage was a correspondingly unsaturated amine. Imines can arise as a result of double-bond isomerization or as a result of β-elimination from metal alkylamides.

Examples of such unsaturated amines having an olefinic C=C double bond are: allylamine, 1-amino-2-butene, 1-amino-3-butene, 1-amino-4-pentene.

To carry out the second process stage in the presence of the hydrogenation or dehydrogenation catalyst (variant a) and b)), a preferred procedure involves passing the product or product mixture from the first reaction stage (hydroamination stage), or the n-butenylamine or enriched n-butenylamine originating from the work-up of the first process stage (hydroamination stage) continuously over the transalkylation catalyst, or transalkylating and optionally hydrating it batchwise.

In the case of a continuous procedure, the transalkylation catalyst is incorporated into a tubular reactor or tube-bundle reactor.

In the case of a transalkylating dehydrogenation/hydrogenation reactor and the procedure in the presence of $H_2$ (variant b), the catalyst can, if desired, be reduced beforehand with hydrogen, although it can also be introduced directly in the presence of the product and hydrogen.

The hydrogen pressure (variant b) can be chosen between 0 bar and 300 bar, preferably between 1 and 250 bar.

For a reaction in the gas phase, the pressure is generally 1 to 70 bar.

For a reaction in the liquid phase, the pressure is generally 70 to 250 bar.

The temperature (variant a and b) is generally 80 to 400° C, in particular between 100 and 350° C., preferably between 120 and 250° C., very particularly preferably between 150 and 230° C.

Depending on the temperature chosen, a thermodynamic equilibrium of the n-butenylamines or n-butylamines, according to the process, plus, possibly, ammonia is established which is dependent on the ratio of nitrogen to the butyl or butenyl groups. The more sterically demanding the amines, the lower the proportion of the corresponding tertiary n-butenylamine or n-butylamine.

The space velocity of starting material over the catalyst can be between 0.05 and 2 kg of starting material per liter of catalyst and per hour (kg/l*h), preferably between 0.1 and 1 kg/l*h, particularly preferably between 0.2 and 0.6 kg/l*h.

The molar ratio of the n-butenylamines or n-butylamines (the "transalkylation reagents") can vary within wide ranges depending on the desired product mix.

In the case of a batchwise transalkylation, the catalyst can be introduced together with the starting material for the second process stage, and the desired amount of transalkylation reactant can be added thereto or replenished. The mixture is then heated to the desired temperature (see above).

Following decompression, the discharge can be worked up by customary methods, e.g. distilled.

In a particular process embodiment, the product mixture obtained in the second process stage (transalkylation and hydrogenation) is separated into (a) product(s) which is/are returned to the first process stage (hydroamination), and/or (a) product(s) which is/are returned to the second process stage (transalkylation and hydrogenation), and the desired n-butylamine(s).

According to the invention, it is also possible to prepare n-butylamines by firstly preparing n-butenylamines as already described by reacting 1,3-butadiene in the form of a 1,3-butadiene-containing mixture obtained during the cracking of petroleum fractions or during the dehydrogenation of LPG or LNG or from GTL technology with a primary amine and/or a secondary amine under hydroaminating conditions and subsequently reacting the resulting hydroamination product(s) in a second process stage under transalkylating conditions, and reacting said n-butenylamines in a further process stage under hydrogenating conditions.

This further process stage under hydrogenating conditions can be carried out e.g. as already described above by corresponding reaction of the n-butenylamine(s) in the presence of a hydrogenation or dehydrogenation catalyst and hydrogen.

The radicals $R^1$ to $R^5$ in the formulae II and III are, independently of one another:

$R^1$, $R^3$, $R^4$:
 hydrogen (H), $R^1$, $R^2$, $R^4$, $R^5$:
 alkyl, in particular $C_1$- to $C_{20}$-alkyl, preferably $C_1$- to $C_{12}$-alkyl, particularly preferably $C_1$- to $C_8$-alkyl, such as methyl, ethyl, n-propyl, isopropyl, n-butyl, isobutyl, sec-butyl, tert-butyl, n-pentyl, isopentyl, neopentyl, n-hexyl, isohexyl, n-heptyl, isoheptyl, n-octyl and isooctyl,
 alkenyl, in particular $C_2$- to $C_{20}$-alkenyl, preferably $C_2$- to $C_{12}$-alkenyl, particularly preferably $C_2$- to $C_8$-alkenyl, such as vinyl and allyl,
 cycloalkyl, in particular $C_3$- to $C_{20}$-cycloalkyl, preferably $C_3$- to $C_{12}$-cycloalkyl, particularly preferably $C_5$- to $C_8$-cycloalkyl, such as cyclopentyl, cyclohexyl, cycloheptyl and cyclooctyl,
 alkoxyalkyl, in particular $C_{2-30}$-alkoxyalkyl, preferably $C_{2-20}$-alkoxyalkyl, particularly preferably $C_{2-8}$- alkoxyalkyl, such as methoxymethyl, ethoxymethyl, n-propoxymethyl, isopropoxymethyl, n-butoxymethyl, isobutoxymethyl, sec-butoxymethyl, tert-butoxymethyl, 1-methoxyethyl and 2-methoxyethyl, particularly preferably $C_2$- to $C_4$-alkoxyalkyl, aminoalkyl, in particular $C_{1-20}$-aminoalkyl, preferably $C_{1-8}$-aminoalkyl, such as aminomethyl, 2-aminoethyl, 2-amino-1,1-dimethylethyl, 2-amino-n-propyl, 3-amino-n-propyl, 4-amino-n-butyl, 5-amino-n-pentyl, N-(2-aminoethyl)-2-aminoethyl and N-(2-aminoethyl)aminomethyl, monoalkylaminoalkyl, in particular $C_{2-30}$-monoalkylaminoalkyl, preferably $C_{2-20}$-monoalkylaminoalkyl, particularly preferably $C_{2-8}$-monoalkylaminoalkyl, such as methylaminomethyl, 2-methylaminoethyl, ethylaminomethyl, 2-ethylaminoethyl and 2-isopropylaminoethyl, dialkylaminoalkyl, in particular $C_{3-30}$-dialkylaminoalkyl, preferably $C_{3-20}$-dialkylaminoalkyl, particularly preferably $C_{3-10}$-dialkylaminoalkyl, such as N,N-dimethylaminomethyl, (N,N-dibutylamino)methyl, 2-(N,N-dimethylamino)ethyl, 2-(N,N-diethylamino)ethyl, 2-(N,N-dibutylamino)ethyl, 2-(N,N-di-n-propylamino)ethyl and 2-(N,N-diisopropylamino)ethyl, aryl, such as phenyl, 1-naphthyl and 2-naphthyl, preferably phenyl, aralkyl, in particular $C_7$- to $C_{20}$-aralkyl, preferably $C_7$- to $C_{20}$-aralkyl, preferably $C_7$- to $C_{12}$-phenalkyl, such as phenylmethyl, 1-phenylethyl, 2-phenylethyl, $R^1$ and $R^2$, $R^4$ and $R^5$:

together are a saturated or unsaturated $C_3$- to $C_9$-alkylene chain which may be interrupted by an O, S or N heteroatom, such as e.g. —$(CH_2)_3$—, —$(CH_2)_4$—, —$(CH_2)_5$—, —$(CH_2)_6$—, —$(CH_2)_7$— and —CH=CH—CH=CH—, together are in particular a —$(CH_2)_j$—X—$(CH_2)_k$ group, where j and k, independently of one another, =1, 2, 3 or 4 and X=$CH_2$, $CHR^3$, oxygen (O), sulfur (S) or $NR^3$, where $R^3$=H or $C_1$- to $C_4$-alkyl, such as methyl, ethyl, n-propyl, isopropyl, n-butyl, isobutyl, sec-butyl, tert-butyl, such as e.g. —$(CH_2)_2$—NH—$(CH_2)_2$—, —$(CH_2)_2$—$NCH_3$—$(CH_2)_2$—, —$(CH_2)_2$—O—$(CH_2)_2$—.

EXAMPLES

Example 1
(Hydroamination of 1,3-butadiene in the Form of a 1,3-butadiene-containing C4 Cut with di-n-butylamine)

50 mmol of Na were melted in 30 ml of anhydrous n-octane at 110° C. and dispersed by stirring. After cooling, 258 g of di-n-butylamine dried over a 3 Å molecular sieve were introduced into a 1 l reactor, the Na suspension was added with the exclusion of oxygen and water, and a C4 cut (235 g) having the composition (in % by weight)

| | |
|---|---|
| 1,3-butadiene: | 42.3 |
| butenes: | 47.5 |
| butanes: | 8.7 |
| alkynes: | 0.8 |
| others: | 0.7 | was introduced, with stirring over the course of 2 h, into the reactor (1 l) via a needle valve.

| Time [min] | Pressure [bar] | C4 cut in g | Temp. [° C.] |
|---|---|---|---|
| 0 | 0 | 0 | 58 |
| 5 | 0.5 | 0.5 | 58 |
| 15 | 1.4 | 16 | 58 |
| 30 | 4 | 44 | 58 |
| 60 | 9 | 120 | 59 |
| 90 | 17 | 195 | 60 |
| 110 | 23 | 235.4 | 57 |
| 135 | 20 | | 61 |
| 180 | 20 | | 62 |

The mixture was then cooled to 50° C., and the gas space was released into a condensation vessel cooled with dry ice/acetone. 10 ml of 50% aqueous KOH were then added to the stirred autoclave (GC analysis: Rtx5 amines, 100° C.–5° C./min–230° C.).

Liquid reactor contents: 344.8 g consisting of:

| Substance | in g | in % |
|---|---|---|
| Di-n-butylamine | 61.9 | 25.0 |
| Di-n-butyl-n-butenylamines | 271.1 | 74.3 |
| Others | | 0.7 |

Condensate: 158 g consisting of:

| GC analysis [Area %] | before | after |
|---|---|---|
| Isobutane | 1.78 | 2.67 |
| n-Butane | 6.02 | 9.41 |
| trans-2-butene | 4.82 | 8.38 |
| 1-Butene | 13.80 | 18.5 |
| Isobutene | 24.4 | 38.9 |
| cis-2-butene | 3.61 | 8.38 |
| Isopentane | 0.040 | 0.041 |
| n-Pentane | 0.027 | 0.02 |
| 1,3-Butadiene | 43.7 | 14.6 |
| Butenine | 0.586 | 0 |
| 1-Butyne | 0.126 | 0 |
| Unknowns (C5+) | 1.09 | 0.32 |

Example 2
(Hydrogenation of the di-n-butyl-n-butenylamine-containing Reaction Discharge Obtained in Example 1)

In a 200 ml autoclave, 40 g of the pale yellow reaction discharge from Example 1 were hydrogenated over an Ni/Co/Cu/$Al_2O_3$ hydrogenation catalyst (10% by weight of CoO, 10% by weight of NiO, 4% by weight of CuO on aluminum oxide; prepared in accordance with DE-A-19 53 263) at 150° C. and a hydrogen pressure of 200 bar for 4 h. The discharge (40.2 g, water-clear) comprised 74.1% of tri-n-butylamine and 25.1 g of di-n-butylamine.

Example 3
(Hydrogenating Transalkylation of the di-n-butyl-n-butenylamine-containing Reaction Discharge Obtained in Example 1)

In a 200 ml autoclave, 20 g of the reaction discharge from Example 1 were charged over an Ni/Co/Cu/$Al_2O_3$ hydrogenation catalyst (10% by weight of CoO, 10% by weight of NiO, 4% by weight of CuO on aluminum oxide; prepared in accordance with DE-A-19 53 263) at 190° C. with 40 ml of ammonia. Hydrogen was then injected to a pressure of 200 bar, and the system was maintained at 190° C. for 4 h. Cooling and slow decompression to atmospheric pressure gave a discharge (22.1 g, water-clear), which comprised 15.2% of mono-n-butylamine, 52.8% of di-n-butylamine, 31.8% of tri-n-butylamine and 0.2% of secondary products (data in GC area %).

We claim:

1. A process for the preparation of n-butenylamines, which comprises reacting 1,3-butadiene in the form of a 1,3-butadiene-containing mixture obtained during the cracking of petroleum fractions or during the dehydrogenation of LPG or LNG or from GTL technology with a primary amine and/or a secondary amine under hydroaminating conditions and subsequently reacting the resulting hydroamination product(s) in a second process stage under transalkylating conditions.

2. A process as claimed in claim 1, wherein the 1,3-butadiene-containing mixture is a C4 cut.

3. A process as claimed in claim 1, wherein the 1,3-butadiene-containing mixture has a 1,3-butadiene content of from 5 to 50% by weight.

4. A process as claimed in claim 1, wherein the 1,3-butadiene-containing mixture comprises less than 2% by weight of hydrocarbons which have a pKa value of less than 30, according to the MSAD scale.

5. A process as claimed in claim 1, wherein the hydroamination is carried out in the presence of an alkali metal as catalyst.

6. A process as claimed in claim 1, wherein the hydroamination is carried out in the presence of sodium as catalyst.

7. A process as claimed in claim 1, wherein the hydroamination is carried out in the presence of a metal monoalkylamide or metal dialkylamide or a metal amide corresponding to the amine used, as catalyst, or in the presence of a transition metal complex compound as catalyst.

8. A process as claimed in claim 1, wherein the hydroamination is carried out in the presence of an alkali metal dialkylamide as catalyst.

9. A process as claimed in claim 1, wherein the hydroamination is carried out in the presence of a sodium dialkylamide as catalyst.

10. A process as claimed in claim 1, wherein the reaction in the second process stage is carried out in the presence of ammonia.

11. A process as claimed in claim 1, wherein the reaction in the second process stage is carried out at temperatures of from 80 to 400° C.

12. A process as claimed in claim 1, wherein the reaction in the second process stage is carried out in the presence of a transalkylation catalyst.

13. A process as claimed in claim 1, wherein the reaction in the second process stage is carried out in the presence of a transalkylating hydrogenation or dehydrogenation catalyst.

14. A process as claimed in claim 1, wherein the product mixture obtained in the second process stage is separated into (a) product(s) which is/are returned to the first process stage, and/or (a) product(s) which is/are returned to the second process stage, and the desired n-butenylamine(s).

15. A process for the preparation of n-butylamines, which comprises preparing one or more n-butenylamine(s) according to claim 1, and reacting it/them in a further process stage under hydrogenating conditions.

16. A process for the preparation of n-butylamines, which comprises carrying out a process according to claim 1, where the reaction in the second process stage is carried out under transalkylating and hydrogenating conditions.

17. A process as claimed in claim 16, wherein the reaction in the second process stage is carried out in the presence of hydrogen and a transalkylating hydrogenation or dehydrogenation catalyst.

18. A process as claimed in claim 16, wherein the reaction in the second process stage is carried out continuously in the presence of a hydrogenation or dehydrogenation catalyst in a fixed bed.

19. A process as claimed in claim 16, wherein the reaction in the second process stage is carried out in the presence of a copper-containing catalyst, which may contain a support material, and hydrogen.

20. A process as claimed in claim 15, wherein the product mixture obtained in the second process stage is separated into (a) product(s) which is/are returned to the first process stage, and/or (a) product(s) which is/are returned to the second process stage, and/or (a) product(s) which is/are passed (returned) to the further process stage (hydrogenation), and the desired n-butylamine(s).

21. A process as claimed in claim 16, wherein the product mixture obtained in the second process stage is separated into (a) product(s) which is/are returned to the first process stage, and/or (a) product(s) which is/are returned to the second process stage, and the desired n-butylamine(s).

22. A process for the preparation of a 1,3-butadiene-free mixture from a corresponding 1,3-butadiene-containing mixture obtained during the cracking of petroleum fractions or during the dehydrogenation of LPG or LNG of from GTL technology, which comprises carrying out a reaction of the 1,3-butadiene-containing mixture with a primary and/or secondary amine according to claim 1.

23. A process as claimed in claim 15 for the preparation of di-n-butylamine and/or tri-n-butylamine using n-butylamine as primary amine.

24. A process as claimed in claim 15 for the preparation of tri-n-butylamine using di-n-butylamine as secondary amine.

* * * * *